United States Patent [19]

King et al.

[11] Patent Number: 4,990,652

[45] Date of Patent: Feb. 5, 1991

[54] INTERMEDIATES FOR PREPARING MULTIFUNCTIONAL THIADIAZOLE LUBRICANT ADDITIVES

[75] Inventors: James P. King, Upper Gwynedd; Sameeh S. Toukan, Phoenixville, both of Pa.

[73] Assignee: Atochem North America, Inc., Philadelphia, Pa.

[21] Appl. No.: 439,759

[22] Filed: Nov. 21, 1989

Related U.S. Application Data

[60] Division of Ser. No. 244,608, Sep. 6, 1988, Pat. No. 4,902,804, which is a continuation of Ser. No. 783,728, Oct. 8, 1985, abandoned.

[51] Int. Cl.$^5$ .................... C07C 69/40; C07C 229/22
[52] U.S. Cl. ............................. 560/192; 560/170; 560/204; 562/567; 562/596
[58] Field of Search ............... 560/170, 192; 562/567, 562/596

[56] References Cited

U.S. PATENT DOCUMENTS

| | | | |
|---|---|---|---|
| 2,760,933 | 8/1956 | Fields et al. | 548/142 |
| 2,836,564 | 5/1958 | Roberts et al. | 548/142 |
| 3,072,669 | 1/1963 | McConnell et al. | 548/127 |
| 3,787,434 | 1/1974 | Volpp et al. | 548/127 |
| 3,910,939 | 10/1975 | Kariyone et al. | 548/127 |
| 3,914,241 | 10/1975 | Elliott et al. | 548/142 |
| 4,177,054 | 12/1979 | Arndt et al. | 71/90 |
| 4,193,882 | 3/1980 | Gemmill | 252/47.5 |
| 4,358,597 | 11/1982 | Fields | 548/142 |
| 4,584,114 | 4/1986 | Gemmill | 252/47.5 |

FOREIGN PATENT DOCUMENTS 0146087 6/1985 European Pat. Off. .
1574430 9/1980 United Kingdom .

*Primary Examiner*—Paul J. Killos
*Assistant Examiner*—Vera C. Clarke
*Attorney, Agent, or Firm*—Bernard F. Plantz

[57] ABSTRACT

The reaction products of the alpha-halogenated half esters or amides of succinic acid and thiadiazole dimercaptides as new compositions of matter and their use as lubricant additives possessing multifunctional properties such as extreme pressure, antiwear, antioxidant and anticorrosion.

5 Claims, No Drawings

INTERMEDIATES FOR PREPARING MULTIFUNCTIONAL THIADIAZOLE LUBRICANT ADDITIVES

This is a divisional of copending application(s) Ser. No. 07/244,608, filed on Sept. 6, 1988, now U.S. Pat. No. 4,902,804, which is a continuation of application Ser. No. 06/783,728 filed on Oct. 3, 1985, now abandoned.

BACKGROUND OF THE INVENTION

This invention relates to the reaction products of the alpha-halogenated half esters or amides of succinic acid and thiadiazole dimercaptides as new compositions of matter and their use as lubricant additives possessing multifunctional properties such as extreme pressure, antiwear, antioxidant and anticorrosion.

Compounds of the present invention have several useful properties as lubricant additives. Most of the literature on oil additives discloses novel compositions which possess one useful property for each invention. For example, U.S. Pat. No. 2,836,564 discloses the condensation products of alpha-halogenated aliphatic monocarboxylic acids and 2,5-dimercapto-1,3,4-thiadiazole as new compositions of matter which possess only one useful property, namely corrosion and/or rust inhibition. In addition, there is nothing in the literature that discloses or suggests the use of the above new compositions as multifunctional lubricant additives.

One of the useful properties according to the present invention is the inhibition of corrosion or rusting of metallic surfaces of equipment employing lubricants, especially in equipment where steam or water is present. As little as a 0.03% concentration in a lubricating media inhibits rusting of metal surface which is in contact with sea water at 60° C. for more than two days. Another useful property to lubricants according to the present invention is reducing wear and friction to metal surfaces of machinery operating under heavy loads, where metal slides against metal, resulting in deterioration of conventional lubricants and excessive wear. The novel additives of the present invention also impart extreme pressure and antioxidant properties to lubricants.

Typical performance data for the products of the invention, including EP, antiwear, and rust inhibition properties are recorded in Table I.

The invention also relates to a number of novel intermediate compounds useful in preparing the thiadiazole lubricant addtive compounds of the invention.

SUMMARY OF THE INVENTION

The compounds of this invention are defined as compounds of the structure $$Z_1-S-Q-S-Z_2,$$

wherein: Q is a bivalent thiadiazole ring moiety selected from the group consisting essentially of 1,3,4-thiadiazole; 1,2,4-thiadiazole; 1,2,3-thiadiazole; and 1,2,5-thiadiazole;

$Z_1$ is 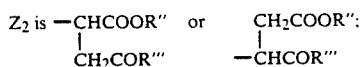

and $Z_2$ is 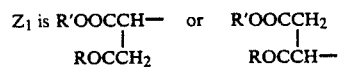

wherein:

R and R''' are each independently selected from the group consisting essentially of hydroxyl, alkoxy, branched or straight chain alkylenoxy of from 2 through 22 carbon atoms, arylalkoxy, OR', NHR', and NR'R';

R' and R'' are each independently selected from the group consisting essentially of hydrogen, alkyl, branched or straight chain alkylene of 1 through 22 carbon atoms, arylalkyl, and heterocyclicalkylene, with the further proviso that at least one of R, R', R'', or R''' forms a carboxyl group with the adjacent carbon atom to which it is linked.

To provide adequate rust inhibition, the compounds of the present invention include at least one carboxyl group. (See, e.g., Example 16).

Preferred compounds are as above, wherein: (1) Q is the 1,3,4-thiadiazole moiety, R' and R'' are hydrogen, and R and R''' are hydroxyl; (2) R and R''' are $-OC_{13}H_{27}$, R' is $C_{13}H_{27}$, R'' is hydrogen, and Q is the 1,3,4-thiadiazole moiety; and (3) R and R''' are $-OC_{13}H_{27}$, R' is $C_{13}H_{27}$, R'' is hydrogen, and Q is the 1,3,4-thiadiazole moiety and the triethylamine, triethanolamine, and tripentylamine salts thereof; (4) R and R''' are $-OC_{13}H_{27}$, R' and R'' are hydrogen, and Q is the 1,2,4-thidiazole moiety; (5) R and R''' are $-OC_{18}H_{35}$, R' and R'' are hydrogen, and Q is the 1,2,4-thiadiazole moiety; (6) R and R''' are $-OC_{18}H_{37}$, R' and R'' are hydrogen, and Q is the 1,2,4-thiadiazole moiety; (7) R' and R'' are hydrogen; R and R''' are NHR'''' or NR''''$_2$ wherein R'''' (can be the same or different) is selected from the group consisting of hydrogen, alkyl, branched or straight chain alkylene of 1 through 22 carbon atoms, arylalkyl, and heterocyclicalkylene; and (8) the compound of (7) wherein R'''' is $-C_{12}H_{25}$.

Among the preferred novel intermediate compounds of the invention are: 4-tridecyl monoester of 2-bromosuccinic acid; ditridecyl 2-bromo-succinate; 4-oleyl monoester of 2-bromo-succinic acid; 4-octadecyl monoester of 2-bromo-succinic acid; and 2-bromo-4-dodecylamino-4-oxobutanoic acid.

Included among the novel oil additive compounds of the invention are those as above defined having a carboxyl group and those compounds wherein the carboxyl group is in the form of an alkali metal or amine salts to enhance the useful properties.

The lubricant of the invention is defined as a major amount of a grease or oil of lubricating viscosity and a minor amount of a compound of the invention as above defined as a lubricant additive to provide enhanced properties to said grease or oil.

DETAILED DESCRIPTION OF THE INVENTION

The new compositions of matter of the present invention are the reaction products of the monoester or monoamide of 2-halosuccinic acid with the alkali metal salts of thiadiazole dimercaptides according to the following equation:

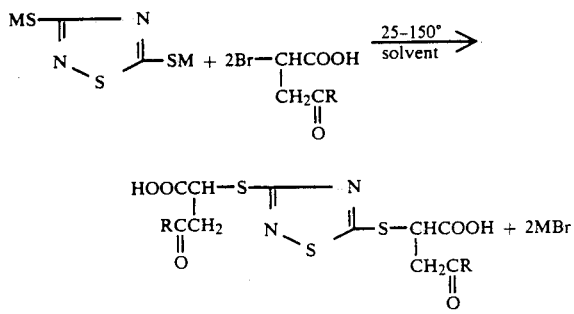

M = Na, K, Li, NH$_4$
R = OR', NHR', NR'$_2$

The thiadiazole dimercaptide can also react with 1 mole of the above monoester or monoamide and 1 mole of the diester or diamide to yield a monocarboxy reaction product having the following structure:

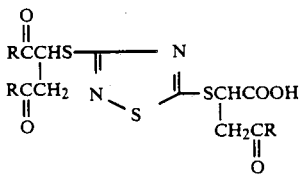

The above reaction products can also be obtained by the addition of thiadiazole dimercaptan (commercially available)

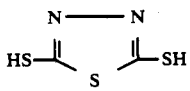

to the ester or amide derivative of maleic acid.

The intermediate ester or amide derivative of succinic acid can be prepared by the reaction of a primary or secondary alcohol or amine with halosuccinic anhydride in a suitable solvent. Among the solvents that can be used are the following: hexane, toluene, THF, and ether. The temperature ranges between 25° to 150° C., preferably 25°–80° C.

Bromosuccinic anhydride can be prepared by refluxing bromosuccinic acid with acetyl chloride followed by distillation of the reaction product. The diester of bromosuccinic acid is prepared by refluxing the acid with 2 moles of the desired alkanol for 7 hours in the presence of a catalytic amount of para toluene sulfonic acid.

Reaction of thiadiazole dimercaptide with the bromosuccinic acid derivative is carried out in ethanol at reflux for 6–12 hours, preferably 8–10 hours. Other solvents can be used such as acetone, acetonitrile, tetrahydrofuran, p-dioxane, etc. The range of the reaction temperature is 25°–150° C. and preferably 70°–100° C.

The following examples are specific embodiments thereof and are not intended to limit the scope of this invention. Structure is confirmed by infrared spectra and in most cases, also by elemental analysis.

EXAMPLE 1

Preparation of [(1,3,4-thiadiazol-2,5-diyl)dithio]-bis(2,2'-succinic acid)

About 68 g. of a solution of 39.6 g. (0.6 mole) of KOH (85%) in 200 ml. of abs. ethanol is added to a stirred slurry of 15.0 g. (0.1 mole) of 2,5-dimercapto-1,3,4-thiadiazole in 80 ml. of abs. ethanol, at 10°–15° C. The resultant mixture is stirred at 10°–15° C. for half hour thereafter, a clear solution of 39.4 g. (0.2 mole) of bromosuccinic acid in 70 ml. of abs. ethanol is added dropwise over a period of 15 minutes at 10°–15° C. followed by the gradual addition of the remainder of the KOH solution at the same temperature range over a period of 15 minutes. After adding 100 ml. of abs. ethanol, the reaction mixture is stirred in the cooling bath for more than one hour, then overnight in water bath at ambient temperature.

The white emulsion-like reaction mixture is refluxed for 6 hours. The hard insoluble solid at bottom of reaction flask is removed by the decantation, dissolved in 500 ml. of distilled water and filtered. pH of filtrate is approximately 8. The filtrate is cooled to 15° C. then acidified with 20% HCl to pH 1.

The acidified aqueous solution is stripped to remove water and volatiles at 60° C. and 5 mm. pressure and the resultant 87.9 g. of an off-white solid residue (slightly wet) is extracted with 3×80 ml. portions of hot acetone. The unextracted solid is dried at about 50° C. and a reduced pressure of 30–50 mm. Hg to obtain 45.3 g. of a white solid which is mostly inorganic salt.

The acetone extract is treated with charcoal then heated on a steam bath to remove solvent. The reddish brown, very viscous residue is again extracted with ether then with tetrahydrofuran and the extract is filtered by gravity to remove 0.5 g. of white solid (discarded).

The clear filtrate is heated on a steam bath and the reddish residue is dried at 100° C. for 8 hours under reduced pressure to obtain 77% yield of a light yellow solid product of this example; m.p. 135°–145° C. (opaque). It is soluble in H$_2$O and acetone.

Anal. Calc'd: C, 31.4; H, 2.64; N, 7.33; S, 25.1. Found: C, 31.8; H, 2.76; N, 6.51; S, 23.5.

EXAMPLE 2

Preparation of 4-tridecyl ester 2-bromosuccinic acid

A mixture of 18.4 g. (0.103 mole) of bromosuccinic anhydride, 21.6 g. (0.108 mole) of tridecanol and 100 ml. of tetrahydrofuran is stirred at ambient temperature for 1.5 hours then refluxed for 3 hours. The clear reaction mixture is stripped at 60° C. under reduced pressure to obtain 99.6% yield of a pale yellowish brown liquid product of this example.

Anal. Calc'd: C, 53.8; H, 8.24; Br, 21.1. Found: C, 54.4; H, 8.35; Br, 20.7.

EXAMPLE 3

Preparation of ditridecyl 2-bromosuccinate

A mixture of 19.7 g. (0.1 mole) of bromosuccinic acid, 40.1 g. (0.2 mole) of tridecanol, 0.25 g. of p-toluenesulfonic acid and 200 ml. of toluene is refluxed for 7 hours, using a Dean-Stark trap. There is collected 3.6 ml. of H$_2$O in the trap which is exactly the calculated amount for this reaction when completed.

The reaction mixture is filtered by gravity and the clear filtrate is stripped at 65° C., 5 mm. pressure to obtain a liquid residue. Drying at about 60° C. under reduced pressure afforded 54.1 (96% yield) of a slightly cloudy liquid product of this example.

An attempt to purify the product by dissolving in hexane, washing with 5% NaHCO$_3$ solution followed by washing 2× with water, removing the solvent on steam bath and drying the residue at 60° C. under reduced pressure fails to give a clear colorless liquid product. Heating the sample at 100° C. for 4 hours also fails to have any effect. No attempt is made to distill the crude product. However, the infrared spectrum is in agreement with the required structure.

EXAMPLE 4

Preparation of tris(tridecyl ester) [1,3,4-thiadiazol-2,5-diyl)dithio]-bis (2,2'-succinic acid)

A monopotassium mercaptide of 2,5-dimercapto-1,3,4-thiadiazole is prepared by the slow addition of a solution of KOH in methanol to a slurry of 2,5-dimercapto-1,3,4-thiadiazole in methanol followed by refluxing for 15 minutes and using 1:1 molar ratio. Filtration of the dark reddish reaction mixture and stripping the solvent off at about 50° C. and 20-30 mm. vacuum affords the greenish yellowish solid of monopotassium salt in 95% yield.

A solution of 14.05 g. (0.025 mole) of ditridecyl 2-bromosuccinate in 100 ml. abs. ethanol is added all at once to a stirred slurry of 4.7 g. (0.025 mole) of the above monopotassium mercaptide in 50 ml. of abs. ethanol. The mixture is then refluxed for 8 hours and filtered. The white precipitate is washed twice with small portions of cold abs. ethanol, adding washing to filtrate. Weight of the dried precipitate is 2.6 g. Calculated amount of KBr by-product is 3.0 g.

The filtrate is cooled in ice to 5°-8° C. before the addition of a solution of 1.65 g. (0.025 mole) of KOH in 40 ml. of abs. ethanol. The temperature of stirred mixture rose to 12° C. The ice bath is removed and stirring continued at ambient temperature for 0.5 hour. A solution of 9.5 g. (0.025 mole) of 4-tridecyl 2-bromosuccinic acid in 10 ml. of abs. ethanol is added dropwise to the stirred reaction mixture followed by refluxing for 12 hours. The white precipitate is filtered off, washed several times with hexane and then dried to weigh 2.7 g. (calc'd KBr 3.0 g.).

The clear filtrate is stripped at 60° C. and 10 mm. pressure to remove the solvent. There is obtained 25.4 g. of a light yellowish brown viscous liquid residue which is dissolved in 150 ml. of hexane. The resulting solution is washed three times with tap water and saturated solution of sodium chloride to break the emulsion. After drying with anhydrous sodium sulfate, the washed hexane solution is stripped as above and the residue is dried at 50° C. under reduced pressure to obtain 22.0 g. (91.8% yield) of a light yellowish brown slightly viscous liquid product of this example. The result of antioxidant properties in a paraffin oil is recorded in Table II.

Anal. Calc'd: C, 63.3; H, 9.54; N, 3.01. Found: C, 63.1; H, 9.43; N, 2.83.

EXAMPLE 5

Preparation of bis(4,4'-tridecyl ester) [(1,3,4-thiadiazol-2,5-diyl)dithio]-bis(2,2'-succinic acid)

A dipotassium dimercaptide of 2,5-dimercapto-1,3,4-thiadiazole is prepared by reacting 3.8 g. (0.025 mole) of 2,5-dimercapto-1,3,4-thiadiazole with 3.3 g. (0.05 mole) of potassium hydroxide in 100 ml. of abs. ethanol, following the procedure of Example 4.

A solution of 19.0 g. (0.05 mole) of 4-tridecyl 2-bromosuccinic acid (Example 2) in 50 ml. of abs. ethanol is added dropwise to the above stirred dipotassium mercaptide solution over a period of 15 minutes. After stirring for a few minutes, an additional 50 ml. of abs. ethanol is added and the resulting mixture is refluxed for 6 hours. The white precipitate is filtered off and washed several times with cold abs. ethanol, then dried at 60° C. under reduced pressure to obtain 5.35 g. of white solid (calc'd KBr=5.95 g.). The filtrate, combined with ethanol washing, is stripped to remove solvent at 65° C. and 1 mm. pressure. There is obtained 19.7 g. of viscous liquid residue which is redissolved in 200 ml. of hexane resulting in a cloudy solution. Filtration by gravity does not clarify the solution completely. The filtrate is washed with water, dried and stripped as in Example 4 to obtain 16.9 g. (93% yield) of a viscous liquid which solidified on standing to an off-white soft solid product of this example.

Anal. Calc'd: C, 57.9; H, 8.37; N, 3.75. Found: C, 58.2; H, 8.68; N, 3.54.

EXAMPLE 6

Preparation of the triethylamine salt of bis(4,4'-tridecyl ester) [(1,3,4-thiadiazol-2,5-diyl)dithio]-bis(2,2'-succinic acid)

A solution of 0.51 g. (0.005 mole) of triethylamine in 25 ml. of hexane is added gradually to a stirred solution of 1.8 g. (0.0025 mole) of the product in Example 5, in 100 ml. of hexane. At once, the mixture becomes cloudy and is stirred at ambient temperature overnight. Thereafter, it is refluxed for 2 hours. A small viscous bottom layer is separated, washed with hexane and dried to obtain 1.7 g. of a viscous light yellowish brown material which is soluble in water and in acetone. Infrared spectrum indicates an amine salt for this product (B). The hexane layer is heated on a steam bath to obtain a soft colorless residue; the weight after drying at 60° C. under reduced pressure is 0.5 g. (A). By-product (A) is soluble in hexane and in oil but insoluble in water. It is believed to be an amide derivative but its structure is not determined.

EXAMPLE 7

Preparation of the triethanolamine salt derivative

Experiment of Example 6 is repeated except substituting triethanolamine for triethylamine and tetrahydrofuran for hexane. There is obtained a light yellowish brown semi-solid material, soluble in water and in acetone but insoluble in hexane or oil. Infrared spectrum is in agreement with the structure of a salt reaction product.

EXAMPLE 8

Preparation of tripentylamine salt derivative

Experiment of Example 6 is again repeated except substituting tripentylamine for triethylamine. There is obtained 100% yield of a dark, slightly viscous, yellowish brown material. The product is insoluble in water, soluble in acetone and partially soluble in paraffinic mineral oil.

EXAMPLE 9

Preparation of bis(4,4'-tridecyl ester) [(1,2,4-thiadiazol-3,5-diyl)dithio]-bis(2,2'-succinic acid)

Example 5 is repeated using the same quantities, procedure and reactants except the dipotassium dimercaptide of 1,2,4-thiadiazole (prepared according to procedure of W. A. Thaler and J. R. McDivitt; J. Org. Chem. 36, 14–18 (1971) is substituted for the 1,3,4-thiadiazole dimercaptide and the reflux time is 8–9 hours. There is obtained 17.3 g. (95% yield) of a light yellowish brown viscous liquid product of this example. It is soluble in acetone and hexane but partially in $H_2O$.

Anal. Calc'd: C, 57.9; H, 8.37; N, 3.75. Found: C, 58.2; H, 8.49; N, 3.28.

EXAMPLE 10

Preparation of 4-oleyl ester 2-bromosuccinic acid

Experiment of Example 2 is repeated using oleyl alcohol and the following quantities: 17.9 g. (0.1 mole) of 2-bromosuccinic anhydride, 28.2 g. (0.105 mole) of oleyl alcohol and 100 ml. of tetrahydrofuran. There is obtained 45.2 g. of a medium dark yellowish brown liquid product of this example that is contaminated with small amount of unreacted oleyl alcohol.

Anal. Calc'd: C, 59.1; H, 8.79; Br, 17.9 Found: C, 59.7; H, 9.06; Br, 16.6

EXAMPLE 11

Preparation of 4-octadecyl ester 2-bromosuccinic acid

Similar to Example 10, the octadecyl derivative is prepared using only 1% molar excess of octadecanol. There is obtained 44.7 g. (99.5% yield) of a light tan waxy solid product of this example.

Anal. Calc'd: C, 58.8; H, 9.19; Br, 17.8. Found: C, 58.6; H, 8.8; Br, 17.5.

EXAMPLE 12

Preparation of bis(4,4'-oleyl ester) [(1,2,4-thiadiazol-3,5-diyl)dithio]-bis(2,2'-succinic acid)

Experiment of Example 9 is repeated except that the oleyl ester of bromosuccinic acid (Example 10) is substituted for the tridecyl ester of bromosuccinic acid. There is obtained a light yellowish brown viscous liquid product of this example in 90% yield. It is soluble in acetone and in a paraffinic mineral oil. The result on antioxidant properties in a paraffin oil is listed in Table II.

Anal. Calc'd: C, 62.5; H, 8.90; N, 3.17. Found: C, 62.2; H, 8.85; N, 3.12.

EXAMPLE 13

Preparation of bis(4,4'-octadecyl ester) [(1,2,4-thiadiazol-3,5-diyl)dithio]-bis(2,2'-succinic acid)

By repeating experiment of Example 12 and substituting the octadecyl ester derivative of Example 11 for the oleyl ester derivative of Example 10, there is obtained a waxy pale yellowish brown solid product of this example in 84% yield. Melting point, 41°–43° C. It is soluble in hexane and slightly soluble in acetone.

Anal. Calc'd: C, 62.3; H, 9.31; N, 3.16. Found: C, 62.4; H, 9.48; N, 2.82.

EXAMPLE 14

Preparation of 2-bromo-4-dodecylamino-4oxobutanoic acid

A solution of 9.3 g. (0.05 mole) of dodecylamine in 30 ml. of hexane is added dropwise to a stirred mixture of 9.0 g. (0.05 mole) of 2-bromosuccinic anhydride in 70 ml. of hexane at 5°–10° C. over a period of 15 minutes. Reaction is exothermic and the mixture is stirred for an additional 15 minutes while still in cooling bath. As a result, the temperature rises to 15° C. and the reaction takes the appearance of a white emulsion. Hexane (100 ml.) is added and stirring is continued at ambient temperature for 24 hours. The white insoluble solid is filtered off, washed several times with hexane then dried at about 50° C. and reduced pressure to obtain 16.1 g. (89% yield) of a white slightly waxy solid product of this example; m. p. 62°–70° C. (opaque).

Anal. Calc'd: C, 52.8; H, 8.30; Br, 21.9; N, 3.84. Found: C, 53.2; H, 8.78; Br, 23.1; N, 3.96.

EXAMPLE 15

Preparation of [(1,2,4-thiadiazol-3,5-diyl)dithio]-bis[2,2'-(4-dodecylamino-4-oxo)-butanoic acid]

A hot solution of 13.1 g. (0.036 mole) of the monoamide product of Example 14 in 50 ml. of absolute ethanol is added gradually to a stirred mixture of 4.1 g. (0.018 mole) of dipotassium dimercaptide of 1,2,4-thiadiazole, prepared according to procedure of W. A. Thaler and J. R. McDivitt, J. Org. Chem. 36, 14–18 (1971). The resultant mixture gets significantly cloudy and is refluxed for 9 hours. The white insoluble solid is filtered off, washed twice with 2.5 ml. of ice cold abs. ethanol, adding the washing to the filtrate. After drying at 60° C. and reduced pressure, there is obtained 3.7 g. of a white solid which is water soluble and represents 86% of the calculated amount of KBr.

The filtrate is stripped at 60° C. and about 5 mm. pressure to obtain 13.4 g. of a yellowish brown residue which in turn is dissolved in 200 ml. of hot ether giving cloudy solution. A small amount of white solid (discarded) is collected on filtration and the filtrate is washed with 2×100 ml. of water, dried with anhydrous sodium sulfate then heated on a steam bath to remove solvent and volatile material. The residue is finally dried as above to afford 10.1 g. (78% yield) of a yellowish brown slightly soft solid product of this example which is insoluble in water but soluble in acetone.

Anal. Calc'd: C, 57.0; H, 8.43; N, 7.81. Found: C, 57.1; H, 9.33; N, 7.45.

EXAMPLE 16

Bis(ditridecyl ester) [(1,2,4-thiadiazol-3,5-diyl)dithio]-bis(2,2'-succinic acid)

Example 9 is repeated using the same molar ratios, procedure and reactants except ditridecyl 2-bromosuccinate of Example 3 is substituted for 4-tridecyl 2-bromosuccinic acid of Example 2. There is obtained 92% yield of a pale yellow viscous liquid crude product of this example. It is soluble in acetone and hexane but insoluble in water.

Anal. Calc'd: C, 66.98; H, 10.34; N, 2.52. Found: C, 65.7; H, 9.77; N, 1.98.

TABLE I

Performance Data of Additives in a Paraffinic Mineral Oil

| | | Shell Four-Ball Weld Pt., kg ASTM D 2596 | Shell Four-Ball Wear Scar, mm ASTM D 2266 | Rust Inhibition ASTM D 665 A & B |
|---|---|---|---|---|
| | Base Oil* | 80 | 0.80 | Severe rust after 24 hrs. in distilled and sea water. |
| Example 4 | 1% in base oil | 160 | 0.66 | No rust after 48 hrs. in sea water. |
| | 0.05% in base oil | — | — | No rust after 48 hrs. in distilled water. |
| Example 5 | 1.0% in base oil | 160 | — | — |
| | 0.05% in base oil | — | — | No rust after 48 hrs. in sea water. |
| Example 6 | 0.05% in base oil | — | — | No rust after 48 hrs. in sea water. |
| | 0.03% in base oil | — | — | Very slight rust after 48 hrs. in sea water. |
| Example 8 | 0.05% in base oil | — | — | No rust after 48 hrs. in sea water. |
| Example 9 | 1% in base oil | 160 | 0.67 | — |
| | 0.05% in base oil | — | — | No rust after 48 hrs. in sea water. |
| | 0.3% in base oil | — | — | Slight rust after 48 hrs. in sea water. |
| Example 12 | 1% in base oil | 160 | 0.67 | — |
| | 0.05% in base oil | — | — | No rust after 48 hrs. in sea water. |
| | 0.03% in base oil | — | — | Severe rust after 24 hrs. in sea water. |
| Example 13 | 1% in base oil | 160 | 0.66 | — |
| | 0.05% in base oil | — | — | Moderate rust after 24 hrs. in sea water. |
| Example 15 | 0.05% in base oil | — | — | No rust after 48 hrs. in sea water. |
| | 0.03% in base oil | — | — | No rust after 48 hrs. in sea water |
| Example 16 | 0.05% in base oil | — | — | Severe rust in sea water in less than 20 hrs. |

*Base oil: 160 SUS solvent refined paraffinic mineral oil.

TABLE II

Evaluation of Antioxidant Properties of Compositions in a Paraffin Oil by Means of High Pressure DSC at 185° C. and 500 PSI $O_2$

| Composition | Induction Time min. |
|---|---|
| Paraffin Mineral Oil (PMO) | 1.9 |
| 1% Tridecyl ester (Example No. 4) in PMO | 133.4 |
| 1% Dioleyl ester (Example No. 12) in PMO | 107.0 |
| 1% Zinc Diamyldithiophosphate in PMO (Commercial Product) | 109.0 |

We claim:
1. 4-Tridecyl monoester 2-bromo-succinic acid.
2. Ditridecyl 2-bromo-succinate.
3. 4-Oleyl monoester 2-bromo-succinic acid.
4. 4-Octadecyl monoester 2-bromo-succinic acid.
5. 2-Bromo-4-dodecylamino-4-oxobutanoic acid.

* * * * *